United States Patent [19]
Mygatt et al.

[11] Patent Number: 5,931,332
[45] Date of Patent: Aug. 3, 1999

[54] TAMPER-EVIDENT CLOSURE WITH PULL-TAB

[76] Inventors: Leonard T. Mygatt, 12791 Panorama Pl., Santa Ana, Calif. 92705; Mathew O. Chedister, 8495 Donnybrook Cir., Anaheim Hills, Calif. 92808

[21] Appl. No.: 08/796,660

[22] Filed: Feb. 5, 1997

Related U.S. Application Data

[63] Continuation-in-part of application No. 08/615,042, Mar. 12, 1996, abandoned.

[51] Int. Cl.$^6$ ............................. B65D 17/34; B65D 41/46
[52] U.S. Cl. ......................... 220/270; 220/783; 220/793
[58] Field of Search .................................... 220/260, 265, 220/266, 268, 269, 270, 780, 783, 784, 792, 793; 215/47, 46, 250, 253

[56] References Cited

U.S. PATENT DOCUMENTS

| | | |
|---|---|---|
| 3,422,984 | 1/1969 | Foster . |
| 4,171,062 | 10/1979 | Allen et al. . |
| 4,344,545 | 8/1982 | Aschberger et al. . |
| 4,488,658 | 12/1984 | Smith et al. . |
| 4,627,550 | 12/1986 | Dines . |
| 4,643,329 | 2/1987 | Mobberley et al. . |
| 4,721,210 | 1/1988 | Lawrence et al. . |
| 4,819,819 | 4/1989 | Robertson, Jr. . |
| 4,821,913 | 4/1989 | Hidding . |
| 4,878,595 | 11/1989 | Uhlig . |
| 4,881,656 | 11/1989 | Chumley et al. . |
| 4,883,193 | 11/1989 | Christensson . |
| 4,890,758 | 1/1990 | Gailus . |
| 4,966,294 | 10/1990 | Mack et al. . |
| 4,986,430 | 1/1991 | Dutt . |
| 5,020,686 | 6/1991 | Dutt . |
| 5,085,333 | 2/1992 | Dutt et al. . |
| 5,085,339 | 2/1992 | Roth et al. . |
| 5,094,357 | 3/1992 | McKinney . |
| 5,111,954 | 5/1992 | Gaudreault . |
| 5,123,561 | 6/1992 | Gross . |
| 5,170,905 | 12/1992 | Luch . |
| 5,219,087 | 6/1993 | Christensson . |
| 5,224,617 | 7/1993 | Gaudreault . |
| 5,307,948 | 5/1994 | Blackburn et al. . |
| 5,348,184 | 9/1994 | Adams et al. . |
| 5,398,836 | 3/1995 | Luch et al. . |
| 5,507,406 | 4/1996 | Urciuoli et al. . |
| 5,511,679 | 4/1996 | Beck . |
| 5,511,680 | 4/1996 | Kinne . |

OTHER PUBLICATIONS

Photographs of Quaker® Oatmeal pull tab lid (date unknown).
Photographs of Del Monte Lite Fruit Cup® pull tab lid (date unknown).

*Primary Examiner*—Stephen Castellano
*Assistant Examiner*—Niki M. Eloshway
*Attorney, Agent, or Firm*—Knobbe, Martens, Olson & Bear LLP

[57] ABSTRACT

A tamper-evident container system having a lid fitting over a container and a pull-tab attached to the lid along frangible lines. The pull-tab angles inwardly and upwardly from a peripheral rim of the lid and terminates below the topmost portion of the lid. The pull-tab joins to the adjacent walls of the lid rim along thin integrally formed webs which are easily severed upon displacement of the pull-tab to provide highly visible evidence of tampering. The webs extend from an inner section of the rim and across at least a portion of an upper bridge formed on the rim, further enhancing the visibility of any tampering. The pull-tab forms a small angle with a vertical inner wall of a recess of the lid and extends circumferentially around the inner wall without extending above the rim. A sealing ring formed on the lid below the pull-tab enables the container system to be resealed by the consumer after opening. A poppet-style injection molding assembly is used to form the lid which creates a space between the mold parts forming the angled pull-tab prior to release of the lid from an undercutting mold structure.

24 Claims, 7 Drawing Sheets

TAMPER-EVIDENT CLOSURE WITH PULL-TAB

CROSS-REFERENCE TO RELATED APPLICATION

The present application is a continuation-in-part of U.S. application Ser. No. 08/615,042, filed on Mar. 12, 1996, now abandoned.

BACKGROUND OF THE INVENTION

1. Field of the Invention

The present invention relates to tamper-evident containers and, more particularly, to a container having a closure which can be opened with a pull-tab attached to the closure along frangible lines, and tooling for manufacturing such a closure.

2. Description of Related Art

Retail containers for food or perishable items having tamper-evident closures or lids have been in regular usage for many years. In most cases, these containers are constructed for use with removable lids which positively seal the container closed during handling and shipping. The lids permit the purchaser to easily open the container, and then reapply the lid to reseal the container and store the remaining contents. For the consumer, evidence of tampering with the container or lid must be highly visible to quickly and reliably assess whether the contents have been potentially contaminated. The visibility of tampering is also important for the packager of the container from a marketing standpoint. For the manufacturer, the visibility of tampering is only one factor to consider, with the ease of manufacture also being a prime consideration.

Many prior art tamper-evident containers and lids are complex, relatively expensive to manufacture designs which employ lid locking structures and tear strips permitting removal of the lid locking structures in a way which make the tampering evident to the consumer. Existing designs employ either a tear-away or breakaway segment on the skirt of the lid, or on the container, which when removed allows access to the lid skirt for lifting the lid and opening the container. Tear-away lid skirt designs do not allow for effective liquid-tight reclosure, and are, in some instances, difficult to reapply and subsequently remove from the container.

Prior lids and containers are frequently formed from injection molded parts, which have complicated molded-in locks and tear strips formed by lines of weakness or frangible sections formed in the lids. Many lids are injection molded from a thermo-setting polymer, such as polyethylene. The lids are molded within a one-piece mold cavity and a one-piece mold core. The walls of the mold cavity form the external surface of the lid, and the walls of the mold core form the internal surface of the lid. Such a mold apparatus is shown in U.S. Pat. No. 4,691,501.

The capital expense required by the container manufacturer for production tooling is often prohibitively high. Moreover, because of the complex structure of the tamper evident locking apparatus, many lids include undercuts for which cam-action tooling must be mechanically activated before ejecting the lid from the mold halves. Such cam action tooling is more expensive than conventional static molds, and introduces production complications, such as timing and duration considerations, and the potential for breakdown.

Another manufacturing concern is that the tamper-evident feature not interfere with use of high speed spinning rod lid application machinery, such as that shown in U.S. Pat. No. 4,691,501.

Some prior tamper-evident container designs include projecting pull-tabs to remove the lid. These pull-tabs often extend outwardly and engage adjacent packages during shipment, so that vibration or other movement may accidentally cause partial removal or loosening of the lids. Additionally, the tamper evident tear strips are sometimes broken, falsely indicating that the container has been opened.

One container with a tamper-evident lid and pull-tab is shown in U.S. Pat. No. 4,627,550. The container includes an inwardly directed pull-tab which is connected to the upper surface of the lid with a plurality of frangible teeth which must be severed to utilize the pull-tab. Given the relatively hidden nature of the frangible teeth, the visibility of tampering is reduced. Indeed, it is conceivable that one could carefully sever the frangible teeth and gain access to the contents of the container, thereafter reattaching the pull-tab to the top surface of the lid without leaving much evidence of tampering. Additionally, the mold used to form the container lid must be relatively complex to release the lid after the frangible teeth are formed.

There is presently a need for an improved tamper-evident container and lid which is easy to manufacture and which includes a highly visible tamper-evident closure arrangement.

SUMMARY OF THE INVENTION

The present invention provides a container and closure which creates a liquid-tight seal before and after initial opening, and provides a clearly visible pull-tab with which to break a tamper-evident web, as well as to use to easily open and reopen the container. The closure cannot be removed without breaking the tamper-evident web which attaches the pull-tab to the closure, as an outwardly projecting shelf on the container has an upwardly extending flange surrounding a skirt depending from the periphery of the closure, preventing the closure from being pried off without evidence of tampering.

In one particular embodiment, the container includes an upper lip surrounding an opening, an outwardly extending shelf surrounding the periphery of the container and joined to the container proximate the lip, and an upwardly extending flange joined to the shelf and spaced from the container. The closure covers the opening in the container and includes a peripheral rim, a bridge, and an outer wall combining to removably secure the closure on the container lip when the closure is covering the opening. The outer wall depends from the bridge and is adapted to fit between the container lip and the flange, a bottom edge of the outer wall terminating proximate to the shelf so that the bottom edge cannot easily be manually engaged to remove the closure from the container. The closure further includes a pull-tab extending inwardly from the peripheral rim and joined to the closure by at least one leg. A frangible web is formed in the closure beginning at a point where the leg is joined to the closure, the web extending at least partially across the bridge of the peripheral rim. The web is adapted to tear upon pulling the pull-tab upwardly and outwardly so as to provide a visible indication that the closure protection has been voided.

In another aspect, the present invention provides a closure for use on a tamper-evident container having an opening and a lip surrounding the opening. The closure comprises a bridge which covers the container lip when the closure is covering the opening, a skirt which depends from the periphery of the bridge, a pull-tab extending inwardly and joined to the closure by at least one leg, and a frangible web formed in the closure and beginning at the point where the leg is joined to the closure. The web extends at least partially across the bridge and is adapted to tear upon pulling the pull-tab upwardly and outwardly so as to provide a visible indication that the tamper-evident feature has been activated (or, that the safety of the product should be questioned).

In a still further aspect, the present invention provides a tamper-evident container having an opening, an upper lip which surrounds the opening, an outwardly extending shelf surrounding the entire periphery of the container and joined to the container proximate the lip, and an upwardly extending flange joined to the shelf and spaced from the container. The shelf and the flange have no weakened or frangible portions and are adapted to form a channel within which a skirt which depends from a closure can fit. A bottom edge of the skirt terminates proximate to the shelf so that the bottom edge of the skirt cannot easily be manually engaged to remove the closure from the container.

The present invention further includes a method of removing a closure from a container having an open mouth surrounded by a lip. The closure has a peripheral rim surrounding a recessed solid portion, the rim having an inner wall, a bridge, and an outer wall combining to form a downwardly opening channel adapted to removably secure the closure on the lip of the container with the solid portion substantially covering the open mouth. The method includes providing a pull-tab integrally joined to the closure and extending inwardly from the peripheral rim above the solid portion, the pull-tab joined to the peripheral rim by at least one leg at a frangible web formed in the rim. The method includes severing the frangible web by pulling the pull-tab upwardly and outwardly so as to provide a visible indication that the pull-tab has been tampered with. The closure is removed completely from the container by pulling the pull-tab to disengage the closure rim from the container lip. The open mouth of the container can be resealed by securing the closure on the container so that the solid portion covers the open mouth.

The present invention also provides a mold assembly for injection molding a closure for a tamper-evident container. The closure has a peripheral rim surrounding a solid central portion recessed below the rim, and a pull-tab extending radially inwardly from the rim above the central portion. The mold assembly comprises a fixed cavity member, a cavity poppet, and a core. The cavity member has a mold surface for forming a portion of the closure of which a segment defines a first side of the pull-tab. The cavity poppet is adapted to translate within a cavity of the cavity member along an axis for a first distance. The cavity poppet has a mold surface for forming a portion of the closure of which a segment defines a second side of the pull-tab opposite the first side. The core is adapted to translate along the axis relative to the cavity member a second distance. The core has a mold surface for forming a portion of the closure, wherein the closure is completely formed between the cavity member, cavity poppet and core. The mold assembly further includes a pair of facing stop surfaces, one on the cavity member and one on the cavity poppet, which limit the relative travel of the cavity poppet within the cavity member along the first direction to a first distance, less than the second distance. The closure is released from the mold assembly by simultaneous translation of the cavity poppet and core along the axis for the first distance to separate the closure from the cavity member. Subsequent translation of the core only to the second distance separates the closure from the cavity poppet.

In a still further embodiment, the present invention includes a method of fabricating a closure having a peripheral rim surrounding a recessed solid central portion, and a pull-tab extending radially inwardly from the rim above the central portion. The fabrication method includes simultaneously forming the closure between mold surfaces provided on a fixed cavity member, a cavity poppet and a core, the cavity member and cavity poppet including opposed mold surface portions which, in combination, form the pull-tab; simultaneously translating both the core and cavity poppet along an axis a first distance to separate the closure and cavity member; restricting the travel of the cavity poppet to the first distance; and translating the core along the axis further than the first distance to a second distance to separate the closure from the cavity poppet.

DETAILED DESCRIPTION OF THE PREFERRED EMBODIMENT

Figure 1:
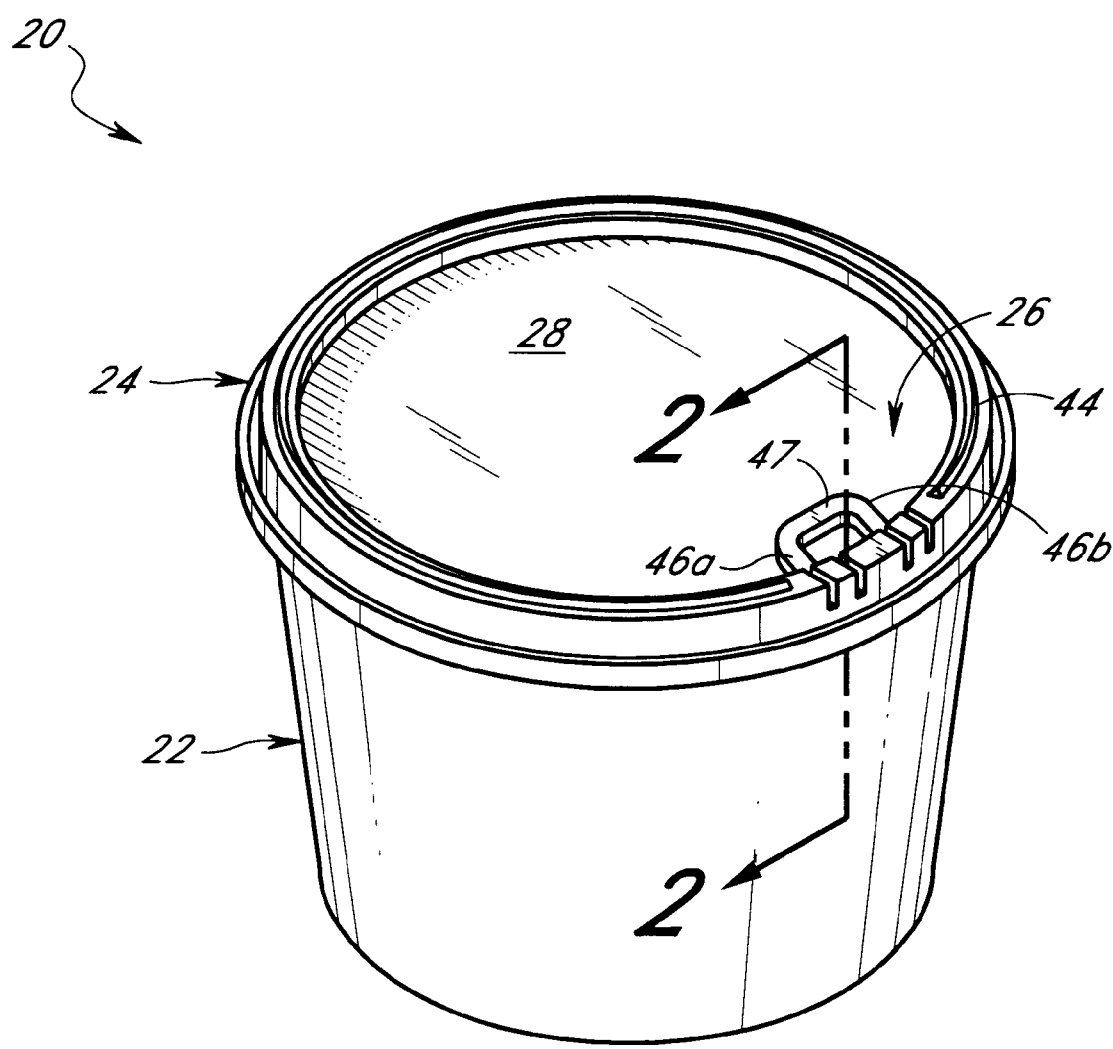
FIG. 1 is a perspective view of a tamper-evident container and closure thereon of the present invention.

With reference to FIG. 1, a tamper-evident container system 20 of the present invention comprises a lower container 22 covered by a closure or lid 24. The container 22 is shown as generally cylindrical with a closed bottom wall and an open-mouthed top connected by a continuous, slightly tapered side wall. The lid 24 conforms to the circular open mouth of the container and is formed in a general disc shape. Of course, the circular configuration is only one possible variation of the container system 20 of the present invention and other cross-sectional container shapes such as rectangular, oval, etc., are contemplated.

Figure 2:
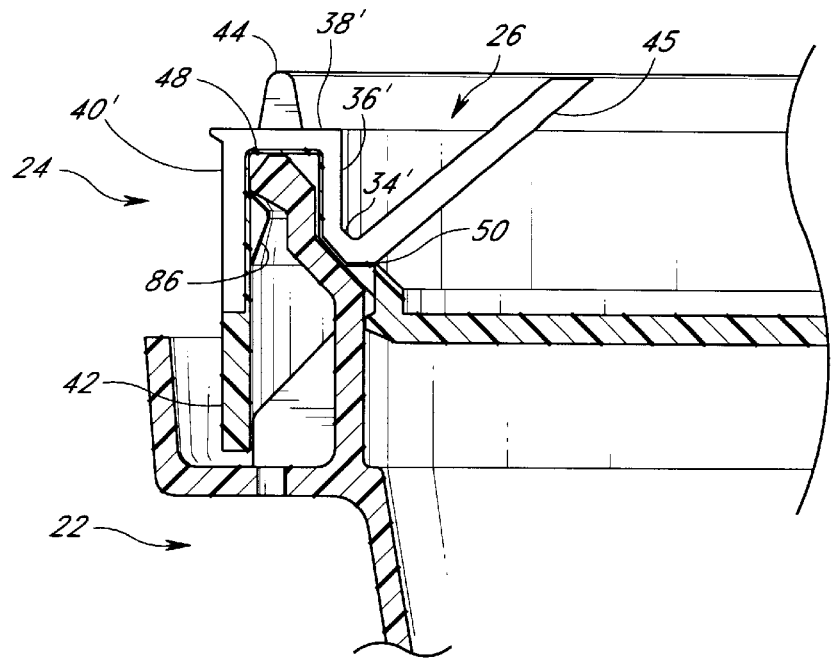
FIG. 2 is a cross-sectional view taken along line 2—2 of FIG. 1 of an upper rim of the container having the closure thereon in its initial, fully sealed position.

With reference to FIGS. 1 and 2, the lid 24 includes a pull-tab 26 integrally molded therewith which allows removal of the lid to open the container 24 and serves as a tamper-evident indicator after the initial opening of the container. Prior to describing the structure of the pull-tab 26 in detail, the overall structure of the lid 24 will be explained.

Figure 2A:
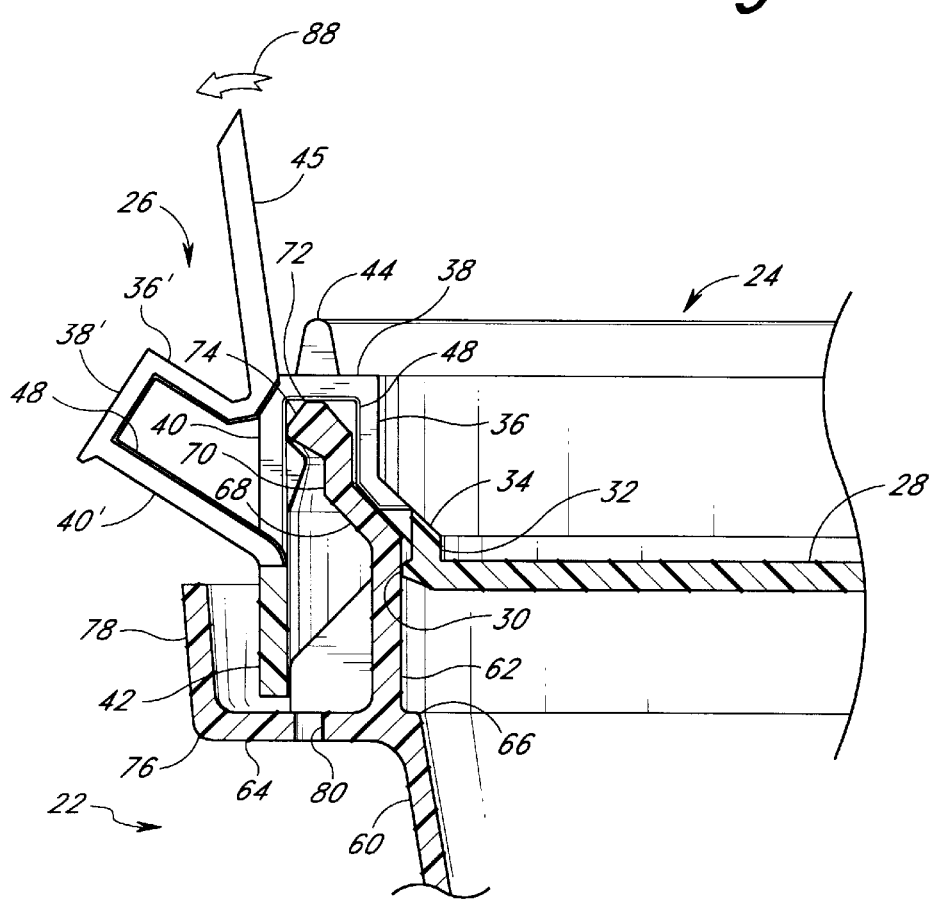
FIG. 2a is a cross-sectional view taken along line 2—2 of FIG. 1 illustrating a pull-tab having been lifted from an initial position during removal of the closure lid from the container.

As seen in FIG. 2a, the lid 24 comprises a central circular disc 28 terminating at its outer periphery in a projecting sealing ring 30. A short first vertical section 32 joins the central disc 28 with an angled portion 34, providing a transition to a second vertical section 36. From the vertical section 36, the lid 24 continues over an upper horizontal bridge 38 and downward along a vertical outer wall 40 to a peripheral skirt 42 defining a lower portion of the outer vertical wall. The combination of the second vertical section 36, bridge 38, and outer wall 40 define a downwardly opening, generally J- or U-shaped, outer rim of the lid 24.

Circular rail 44 forms the uppermost part of the horizontal bridge 38 and extends substantially around the entire lid 24. The utility of the circular rail 44 in stacking and handling of the lid 24 will be more fully explained below. The lid 24 has a continuous cross section around substantially its entire periphery except for a portion proximate the pull-tab 26. At this location, as seen in FIG. 1, the circular rail 44 terminates at two ends.

Figure 5:
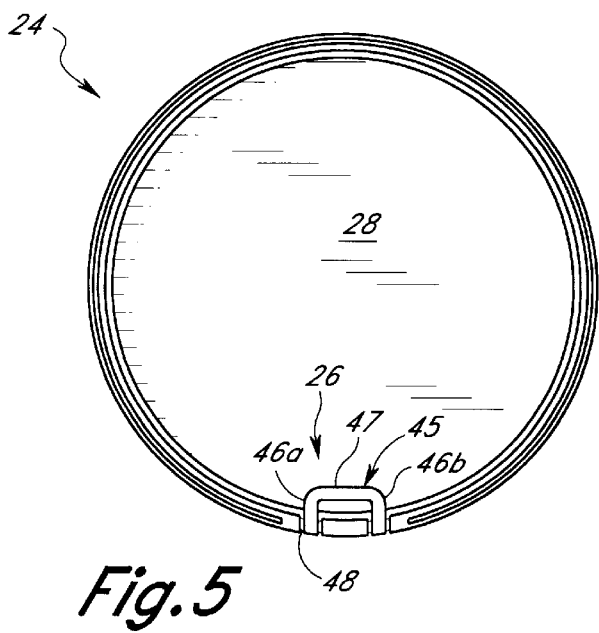
FIG. 5 is a top plan view of the closure lid of the present invention.

With reference to FIGS. 1 and 5, the pull-tab 26 comprises a U-shaped handle 45 having a pair of legs 46a, 46b and a connecting member 47. The legs 46a, 46b define two structural strips which, as seen in FIGS. 2 and 2a, traverse the peripheral rim of the lid 24 in a short angled portion 34', a vertical section 36', a horizontal bridge 38', and a vertical outer wall 40'. All the sections of the legs 46a,b substantially conform in shape and thickness to the correspondingly numbered elements of the main portion of the lid 24. The U-shaped handle 45 angles upwardly and inwardly from the angled portion 34'.

The cross section of FIGS. 2 and 2a is taken through one of the slots formed in the region of the attachment of the pull-tab legs 46a,b to the rest of the lid 24. The pull-tab 26 attaches to the lid 24 along thin webs 48 extending on both sides of the legs 46a,b at their respective junctions with the adjacent lid sections. Thus, there are four such webs 48, one on either side of each leg 46a and 46b. As seen in FIG. 2, each thin web 48 extends from a tear point 50 at the junction between the angled handle 45 and the angled portion 34 of the lid 24 to the approximate mid-point of the outer wall 40, corresponding to the upper end of the peripheral skirt 42. In one embodiment, the thickness of the various walls of the lid 24 and pull-tab 26 range from approximately 0.022 inches (0.56 mm) to approximately 0.028 inches (0.71 mm), while the thickness of the web 48 is approximately 0.003 inches (0.076 mm), or less than about ¼ the thickness of the walls of the lid or pull-tab. Alternatively, the web can be replaced with a portion of material which is weakened by other means, such as perforations or scoring.

The pull-tab 26 may have alternate shapes and may be joined to the lid by more or less than two legs. For example, the pull-tab could also be configured in a T-shape having only one leg joined to the lid 24.

The container 22 comprises a tapered lower wall 60, which splits into a vertical upper wall 62 and a horizontal outwardly extending shelf 64 at a shoulder 66. The upper wall 62 continues upward and tapers outward at a flared portion 68 leading to a short, vertical portion 70 terminating in a thickened upper lip 72. The upper lip 72 exhibits an outwardly facing circular rib 74. The outwardly extending shelf 64 terminates at a bend 76 leading to a generally vertical or slightly outwardly tapered outer flange 78. The shelf 64 and outer flange 78 surround the entire container and preferably have no tear-away portions.

Figure 4:
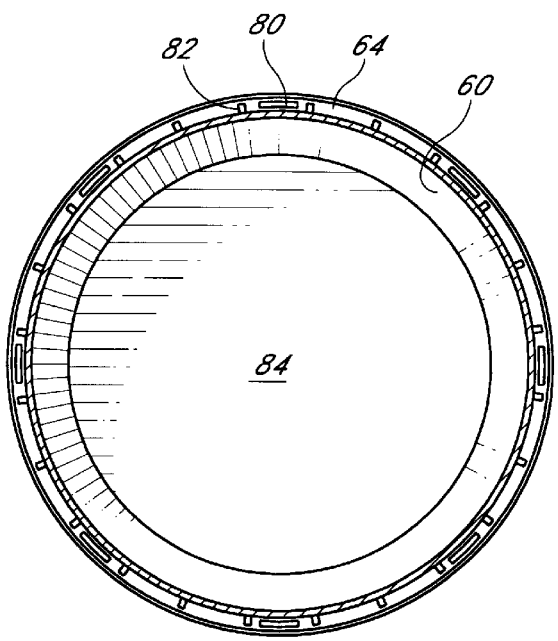
FIG. 4 is a sectional view taken along line 4—4 of FIG. 3 of one of the containers of the present invention.

As seen in FIGS. 2a and 4, a plurality of drainage apertures 80 are formed at evenly spaced circumferential locations through the horizontal shelf 64. The drainage apertures 80 allow for any liquid, such as condensation or water used to clean the container, to drain to prevent the formation of mold or other moisture-related contamination in the channel. Additionally, a plurality of vertically disposed reinforcing gussets 82 extend between an outer surface of the upper wall 62 and the horizontal shelf 64. The container bottom wall 84 is also seen in FIG. 4.

Figure 3:
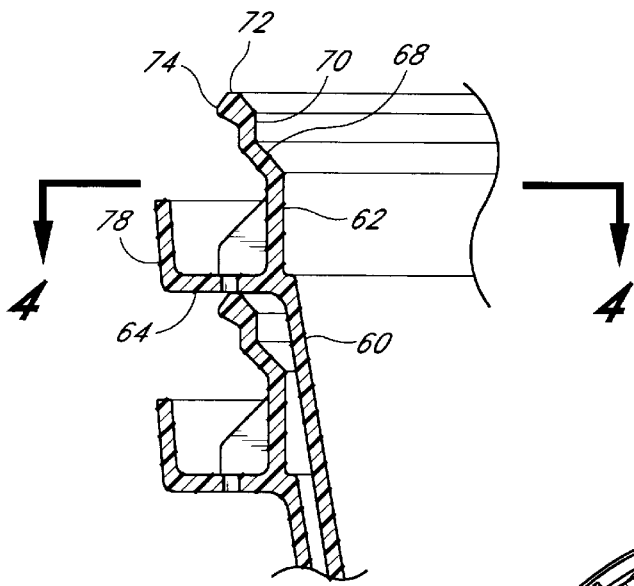
FIG. 3 is a cross-sectional view through the upper rims of a pair of stacked containers of the present invention.

The container 22 is adapted to easily stack with other like containers, as seen in FIG. 3. The upper lip 72 of one container contacts the lower surface of the shelf 64 of the container above. Because of the taper of the lower wall 60, a space is created between adjacent lower walls so that the containers do not bind and can easily be separated for assembly with the lids 24. The reinforcing gussets 82 help strengthen large stacks of containers 22 by preventing the shelf 64 from bending.

The downwardly opening, generally J-shaped peripheral rim of the lid 24 is designed to fit over the upper lip 72 of the mouth of the container 22. An inwardly facing rib 86 formed on the inner surface of the outer wall 40 of the lid 24 cams past the outwardly-facing rib 74 and secures the lid on the container 22. The inwardly facing rib 86 is discontinuous, much like the rail 44, and extends substantially around the circumference of the outer wall 40 except in the region of the pull-tab 26.

The lid 24 is designed to sealingly mate with the upper rim of the container 22. In particular, with the lid 24 secured over the mouth of the container 22, and the ribs 74 and 86 preventing easy removal of the lid, the sealing ring 30 of the lid is positioned in intimate sealing contact with the inner surface of the upper wall 62 of the container. Thus, the central disc 28 completely covers and seals the container opening defined by the upper wall 62.

In an important aspect of the present invention, the lid 24 is relatively difficult to remove from the container 22 without the use of the pull-tab 26. More particularly, the downwardly extending peripheral skirt 42 of the lid terminates at a location close to or touching the upper surface of the horizontal shelf 64. Since the outer flange 78 completely surrounds the bottom end of the peripheral skirt 42, it seriously inhibits any direct lifting of the peripheral skirt and integral lid. To remove the lid 24 by lifting the peripheral skirt 42, one would need to insert a tool into the aperture between the outer flange 78 and the peripheral skirt, and pry the lid upward. This operation would likely result in damage to either the peripheral skirt 42 or outer flange 78, or both, indicating that the contents of the container may have been tampered with. Furthermore, provision of the reinforcing gussets 82 greatly strengthens the horizontal shelf 64, preventing the shelf from being bent downward which would allow easier access to the bottom end of the peripheral skirt 42.

The procedure for initially removing the lid 24 from the container 22 will now be described. The pull-tab handle 45 is initially in the position shown in FIG. 2. The handle 45 is manually grasped and pulled upwardly and outwardly to remove the lid. With reference to FIG. 2a, the handle 45 of the pull-tab 26 is shown after being pulled in the general direction of the arrow 88. The pulling causes severing of the webs 48 at the several tear points 50. More particularly, there are four continuous lines of the web 48 and all are initially severed at the tear points 50 at approximately the same time. The webs 48 continue upward and across the bridge 38 and down the outer wall 40 of the lid 24. The pull-tab 26 is prevented from being severed completely from the lid 24 by the termination of the webs 48 at the peripheral skirt 42. The lower ends of the outer walls 40' of the pull-tab 26 thus transition into and are integral with the annular peripheral skirt 42. FIG. 2a illustrates portions of the thin web 48 still remaining on both the side edge of the leg 46a of the pull-tab 26 and the edge of the adjacent lid 24.

Once the webs 48 have been fully severed and the pull-tab 26 is in the position shown in FIG. 2a, pulling upward on the pull-tab raises that portion of the peripheral skirt 42 at which the pull-tab is attached. This causes the peripheral skirt 42 to swing outward toward the flange 78 releasing the engagement between the ribs 74 and 86 at this location. The entire lid 24 can thus be pulled upward and away from the upper rim of the container 22 using the pull-tab 26.

Subsequently, the lid 24 can be reattached over the opening of the container 22 to reseal the contents along the sealing ring 30. In other words, the severing of the thin web 48 provides a highly visible tamper-evident system, yet the integrity of the lid seal is not compromised, even after repeated openings and closings. This is so because the severing of the webs 48 commences at the previously described tear point 50 at the junction between the angled handle 45 and the angled portion 34 of the lid 24. The tear point 50 is located above the circular sealing ring 30 so as not to deform or otherwise damage the ring. Thus, the present system 20 provides a "double-sealing" capability: once to seal the contents in a tamper-evident manner during shipping and retailing, and a second time to preserve the freshness of the contents after the consumer has opened the system for the first time—both times the lid 24 being removed by using the pull-tab 26.

In a further aspect, the pull-tab 26 remains attached to the lid 24. Namely, the webs 48 terminate at the approximate mid-point of the outer wall 40, corresponding to the upper end of the peripheral skirt 42. The legs 46a,b are thus integral with the peripheral skirt 42 at their lower ends and will not detach therefrom without significant extra force. Because the pull-tab 26 remains attached, the container system 20 may be easily reopened after the initial opening. The integral pull-tab 26 also ensures that the pull-tab does not separate and contaminate the foodstuffs provided in the container 22, or present a choking hazard for small children if accidentally dropped to the ground.

The present container system 20 provides a highly visible tamper-evident locking structure. More particularly, as described above, the pull-tab 26 is the only way of opening the lid 24 from the container 22 without evidence of tampering. The pull-tab 26 can only be utilized by severing the webs 48 so that the peripheral skirt 42 can be lifted. This results in unmistakable evidence of tampering especially in light of the fact the webs 48 extend over the bridge 38 of the lid 24, which portion at least must be severed to utilize the pull-tab 26 and open the container. Once severed, it would be extremely difficult to surreptitiously reconstruct the webs 48 and doctor them in such a way that the container appeared not to have been tampered with. Indeed, the thin web 48 is plastically stretched when severed, resulting in an extremely jagged configuration. Such a reattachment operation would be practically impossible. Not only are the webs 48 severed, but the pull-tab 26 is invariably plastically deformed to some degree so that it no longer conforms to the contours of the lid 24, but instead projects upward therefrom.

The present invention provides several other benefits manifested in the shipping and handling process. More particularly, the inwardly directed handle 45 of the pull-tab 26 cannot be jostled or otherwise moved by objects to the exterior of the closed container system 20. This helps prevent the lid from being inadvertently loosened, or the pull-tab from being severed to falsely indicate that the container has been tampered with. Additionally, as seen in FIG. 2, the upper end of the handle 45 terminates below a plane defined by the apex of the peripheral rim, formed by the circular rail 44. This means that in handling the lids 24, the stacking and sorting machinery can separate the lids relatively easily reducing the potential for snags in the assembly line. In a typical assembly process, the lids 24 are conveyed along a number of rotating support rods, and eventually are dropped down through slots to be joined with the container 22. The slots have a narrow width which is just wide enough to accommodate the lid 24. Thus, by virtue of being below the plane of the rail 44, the pull-tab 26 will not cause the lid 24 to bind in the slots.

Figure 6:
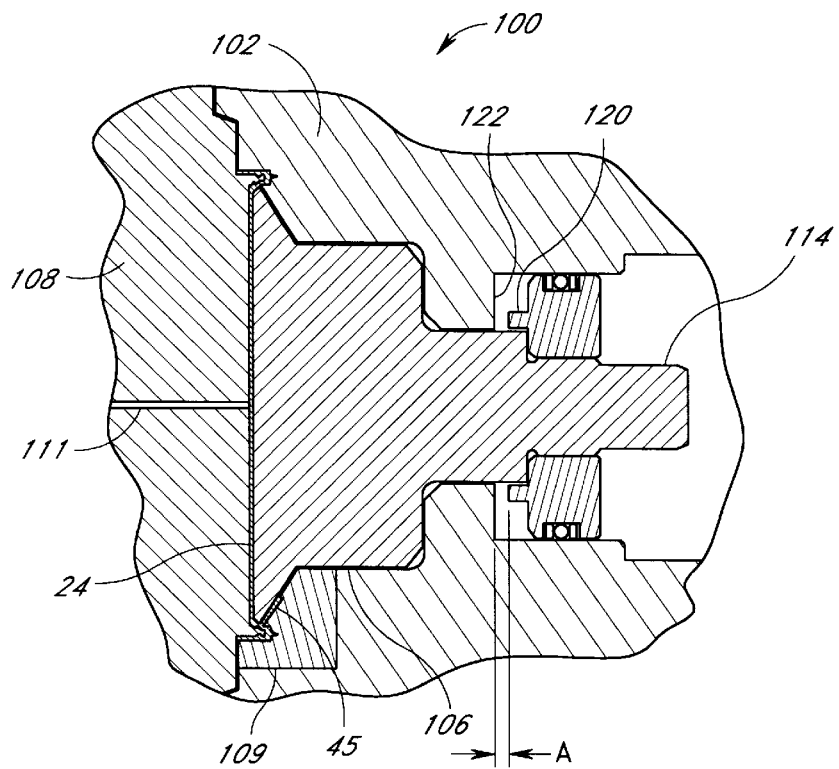
FIG. 6 is a simplified cross-sectional view of a preferred mold assembly for forming the closure lid of the present invention.
Figure 7:
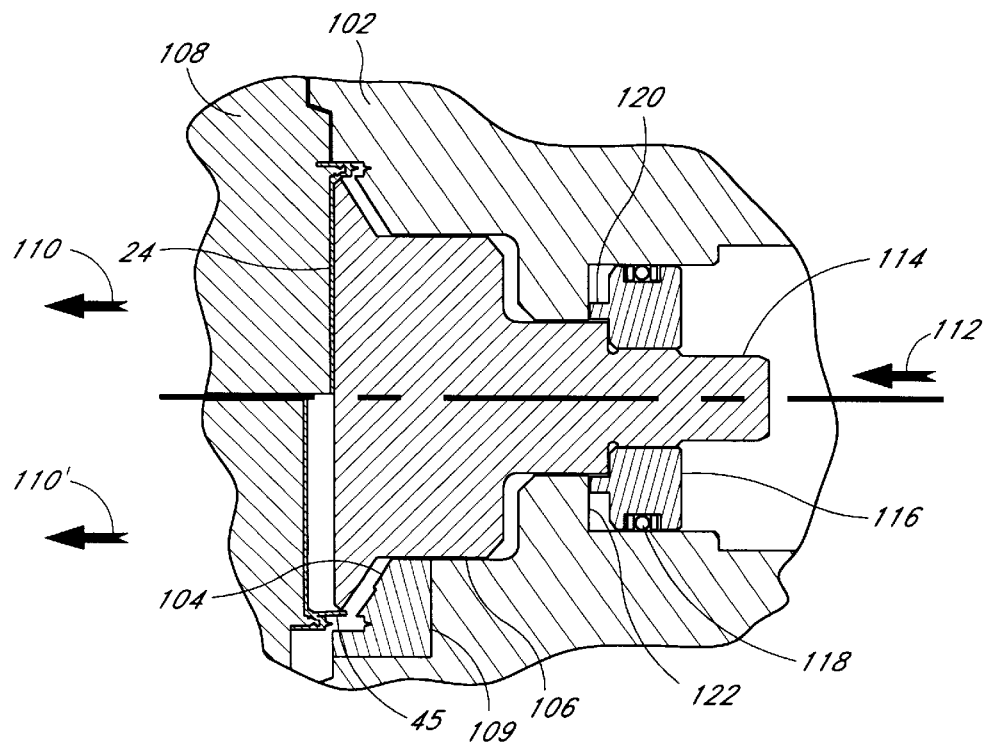
FIG. 7 is the mold assembly of FIG. 6 in use illustrating a preferred poppet-type mold half facilitating removal of the closure lid from the mold assembly.

In another advantageous feature of the present invention, a novel mold assembly is provided that allows the lid 24 to be rapidly and efficiently ejected therefrom. With reference to FIGS. 6 and 7, a simplified mold assembly 100 comprises a fixed cavity member 102 defining a mold cavity 104 therein, a cavity poppet 106, and a core 108. The cavity poppet 106 and core 108 are coaxially arranged in the mold cavity 104 and both are adapted to translate axially therein. The core 108 defines the contours of the inner surfaces of the lid 24, while the combination of the cavity member 102 and cavity poppet 106 define the upper surfaces of the lid. FIG. 6 shows the lid 24 having been formed between the various mold assembly elements. As shown schematically, an injection channel 111 for the liquified polyethylene is preferably provided at the center of the core 108. The channel 111 typically includes a piston-actuated gate assembly for stopping and starting the flow of molten plastic into the mold cavity, although other devices can be substituted.

Preferably, a mold insert 109 is provided in the cavity member 102 defining an arcuate segment of the mold cavity 104 for forming the closure 24. Specifically, the insert 109 defines the portion of the mold cavity 104 which forms the pull-tab 26, including the handle 45, legs 46a,b, and associated webs 48. Because the insert 109 is removably secured within the cavity member 102, it may be replaced to modify the shape of the pull-tab 26. Preferably, the insert 109 is bolted to the cavity member 102.

To remove the formed lid 24, the core 108 is axially retracted in the direction of the arrow 110, as seen in the upper half of FIG. 7. The cavity poppet 106 translates with the core 108, as indicated by arrow 112. This separates the lid 24 from the cavity member 102. The cavity poppet 106 is provided with suitable journals and bearings to slide within the cavity member 102, as will be appreciated by one of skill in the art. The cavity poppet 106 is, in one preferred embodiment, a water-cooled pneumatic piston rod responsive to signals from a timing controller (not shown).

A poppet shaft 114 on one end of the cavity poppet 106 includes outer threads which mate with inner threads on a poppet piston nut 116. The poppet piston nut 116 is provided with an outer bearing 118 to facilitate smooth translation within the cavity member 102. As seen in FIG. 6, the piston nut 116 includes an annular projection 120 which, in an initial position during molding of the lid 24, is axially spaced a distance A from a stop face 122 formed in the cavity member 102.

Upon a predetermined axial translation of both the core 108 and cavity poppet 106, the annular projection 120 contacts the stop face 122, as seen in FIG. 7. Upon contact between the annular projection 120 and the stop face 122, the cavity poppet 106 is prevented from further translation, whereupon the core 108 is translated further to pull the formed lid 24 from the cavity poppet 106, as seen in the lower portion of FIG. 7. The handle 45 is shown as it flexes around the outer periphery of the cavity poppet 106.

Due to the relatively fragile nature of the pull-tab handle 45, the space created between the angled surfaces of the cavity poppet 106 and cavity member 102 is essential in removing the lid 24 without rupturing the handle 45. Because of this space, the pull-tab handle 45 is not closely restrained and may easily flex around the outer periphery of the cavity poppet 106 without rupture. As a result, lids having the present pull-tab design can be manufactured without an increase in production cycle time over traditional lids. Without forming this relief space between the cavity poppet 106 and the cavity member 102, it would be extremely difficult to extract the undercut pull-tab handle 45 from the mold assembly without rupture or using a prior art cam-action tooling design. The amount of relief space created may be adjusted by threading the poppet piston nut 116 over the poppet shaft 114 to vary the initial spacing A between the projection 120 and stop face 122, and thus the travel distance of the poppet 106. In a preferred embodiment, the distance A is 0.100 inch (2.54 mm) which is sufficient to allow the undercut pull-tab handle 45 to be extracted from the mold assembly without rupture.

Figure 8:
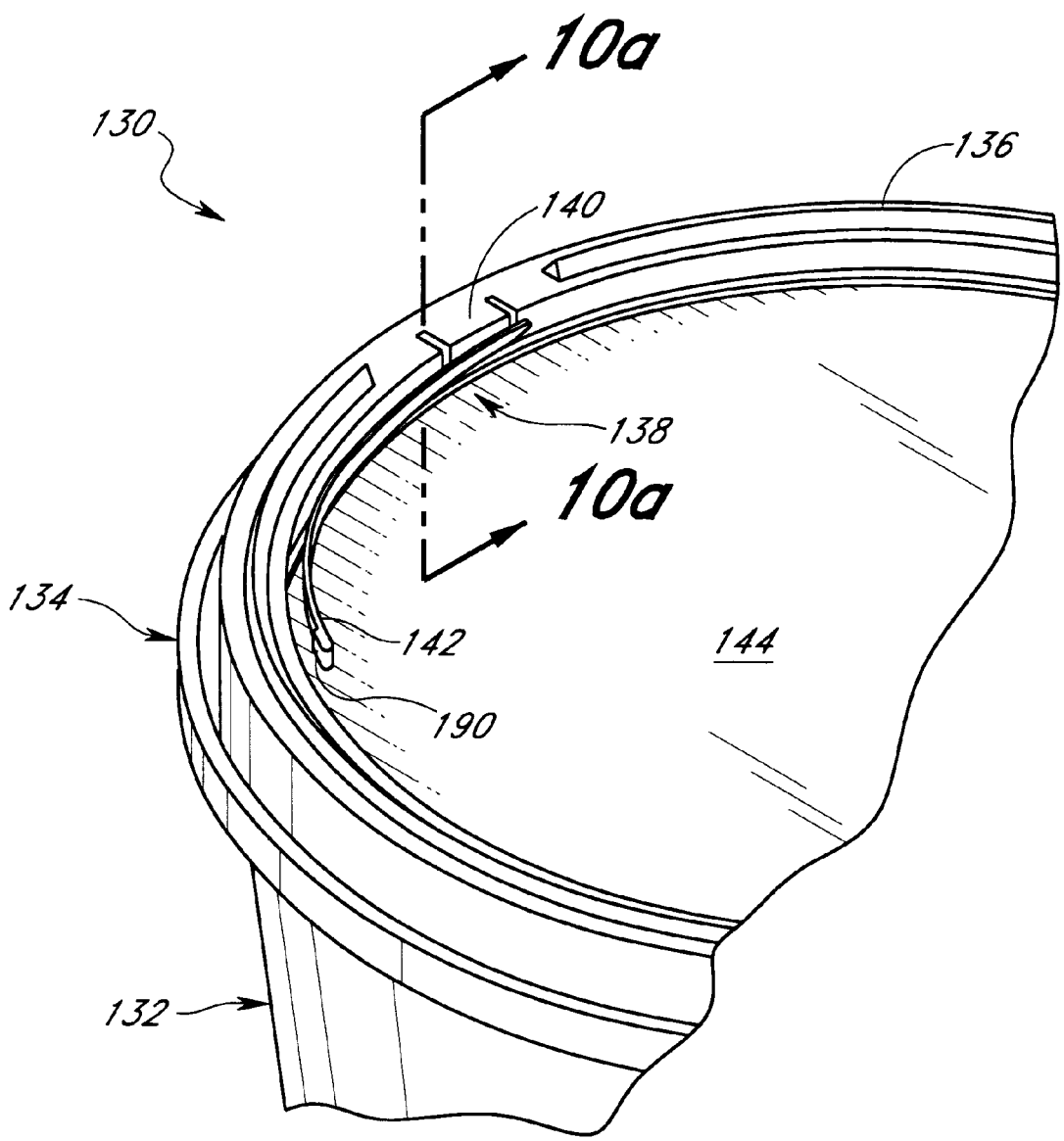
FIG. 8 is a perspective view of an alternative embodiment of a tamper-evident container and closure thereon of the present invention.
Figure 9:
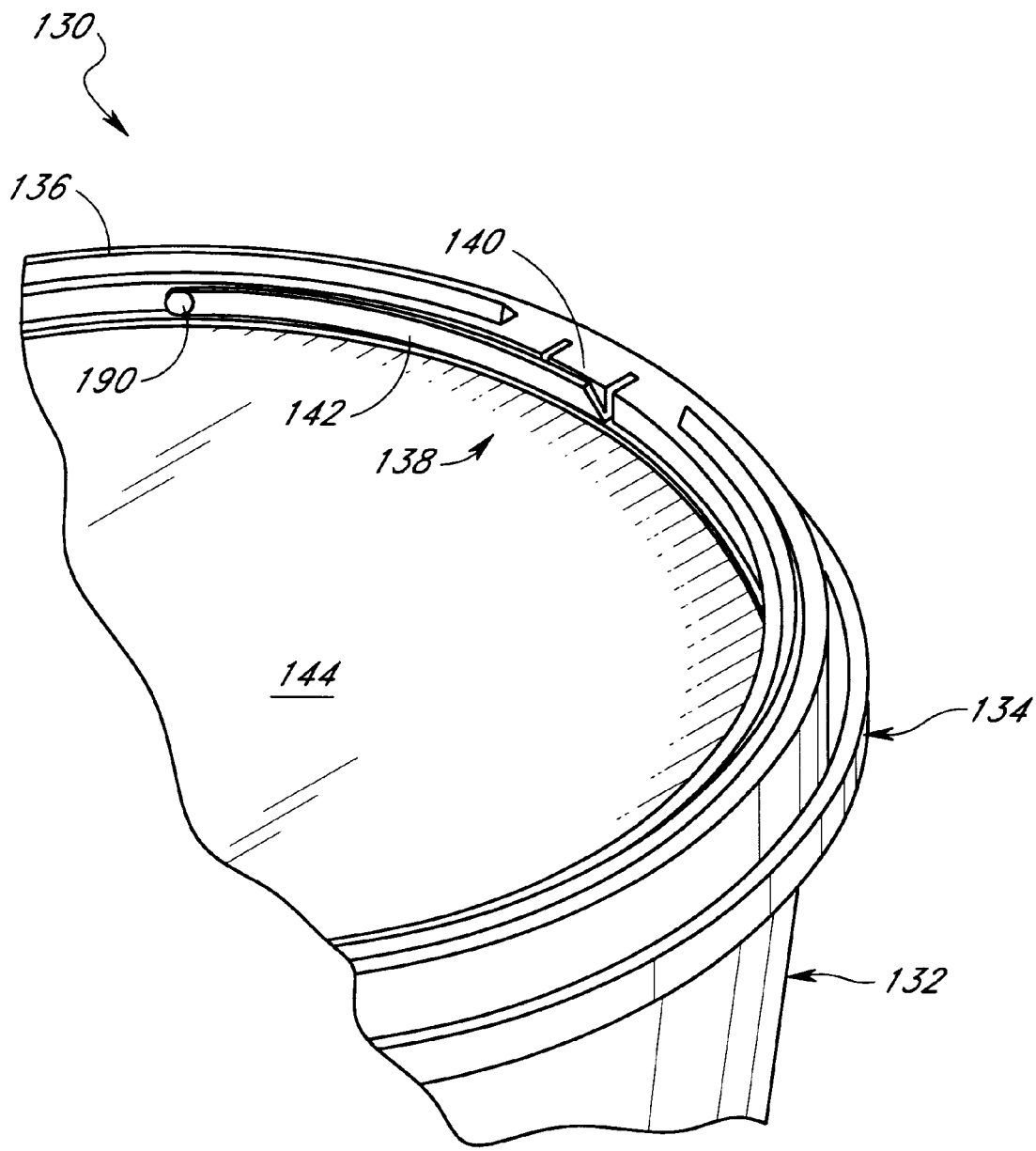
FIG. 9 is a perspective view of the tamper-evident container of FIG. 8 as viewed from a different angle.

FIGS. 8 and 9 illustrates a preferred alternative tamper-evident container system 130 of the present invention, comprising a lower container 132 covered by a closure or lid 134. As in the first-described embodiment, the container 132 is generally cylindrical with a closed bottom wall and an open-mouthed top connected by a continuous, slightly tapered outer sidewall. The lid 134 conforms to the circular open mouth of the container and is formed in a disc shape. Again, other cross-sectional shapes for containers are known, and the alternative configuration can equally be adapted to those container shapes.

In the previous embodiment, a pull-tab 26 for opening the closure angled inwardly and upwardly from an upper rim of the closure. Using the preferred poppet-style mold described with respect to FIGS. 6 and 7, it has been found that flexing of the pull-tab 26 during formation of the closure creates the potential for cracks to form at the structural line of attachment of the pull-tab to the closure. This potential for cracking, even if minimal, may create unacceptable rejection rates during production. Of course, as mentioned above, other types of molds, such as cam-action molds, may be substituted for the poppet-style mold described to eliminate this cracking potential. These types of molds, however, are more complex and more expensive. Therefore, to realize the full advantages of the presently described poppet-style mold of FIGS. 6 and 7, an alternative pull-tab shown in FIGS. 8 and 9 has been developed.

With reference to FIGS. 8 and 9 again, the closure 134 defines an upper rim 136 to which a pull-tab 138 attaches. The pull-tab 138 comprises a single attachment portion or leg 140 and a handle 142. In a similar manner as described for the first embodiment, the leg 140 is weakly attached to at least part of the rim 136, and may be severed therefrom to break the tamper-evident seal on the closure 134 and allow access to the contents of the container 132. In the illustration of FIGS. 8 and 9, the pull-tab 138 is shown fully attached prior to being actuated to open the closure 134. The leg 140 conforms to a cross-sectional shape of the rim 136, and the handle 142 angles inwardly therefrom and extends in a circumferential direction around the inner periphery of the rim 136.

Figure 10A:
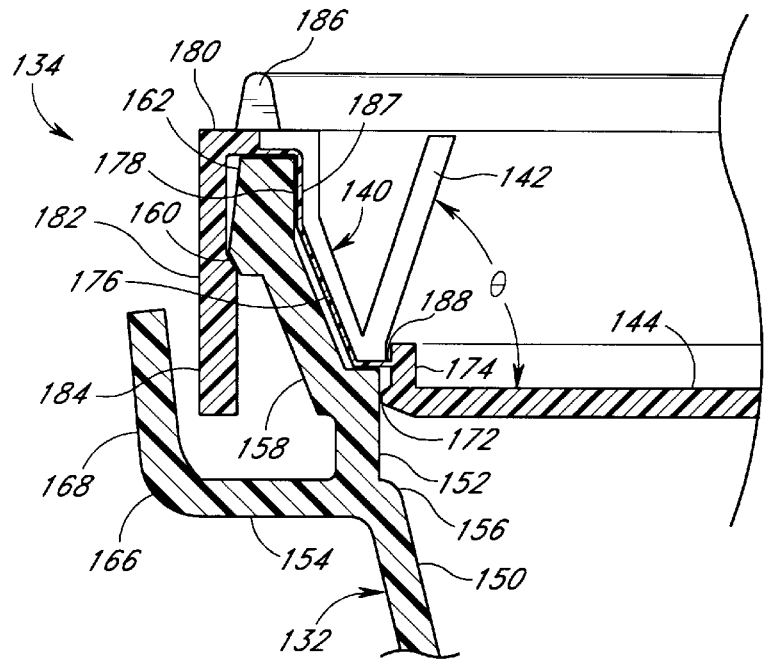
FIG. 10a is a cross-sectional view taken along line 10a—10a of FIG. 8 of an upper rim of a container having the closure thereon in its initial, fully sealed position.

The cross-sectional shape of the upper edge of the container 132 and unopened closure 134 positioned thereon is shown in FIG. 10*a*. As in the previous embodiment, the container 132 comprises a tapered lower wall 150 which splits into a vertical upper wall 152 and a horizontal outer extending shelf 154 at a shoulder 156. The upper wall 152 continues upward and tapers outward at a flared portion 158 leading to a thickened upper lip 162 exhibiting an outwardly facing circular rib 160. The outwardly extending shelf 154 terminates at a bend 166 leading to a generally vertical or slightly outwardly tapered outer flange 168. The shelf 154 and outer flange 168 surround the entire container 132 and preferably include no tear-away or otherwise weakened portions.

The closure 134 includes a central recess having a floor 144 terminating at its outer periphery in a projecting sealing ring 172. A short first vertical section 174 joins the central floor 144 with an angled portion 176, providing a transition to a second vertical section 178. From the vertical section 178, the closure 132 continues over an upper horizontal bridge 180 and downward along a vertical outer wall 182 to a peripheral skirt 184 defining a lower portion of the outer vertical wall. The skirt 184 provides an annular thickened region or inwardly facing ridge for cooperating with the outwardly facing circular rib 160 of the container 132.

A circular rail 186 forms the uppermost part of the horizontal bridge 180 and extends substantially around the entire closure 134. As before, the circular rail 186 facilitates stacking and handling of the closure 134. The closure 134 has a continuous cross-section around substantially its entire periphery, except for a portion proximate the pull-tab 138. At this location, as seen in FIGS. 8 and 9, the circular rail 186 terminates at two facing ends.

Still with reference to FIG. 10*a*, the pull-tab 138 comprises the handle 142 and leg 140. The leg 140 comprises a structural strip having a thickness approximately equal to the rest of the closure, and is defined on circumferentially lateral sides by a pair of parallel webs 187 of reduced thickness by which the leg attaches to the closure. The thickness of the leg 140 and webs 187 are as previously described with respect to the first embodiment. As seen in FIGS. 8 and 9, the leg 140 extends from a location within the recess and proximate the circular floor 144 along the angled portion 176 and second vertical section 178 of the closure to the bridge 180. Preferably, the leg 140 continues radially outward at least partly across the bridge 180, and more preferably, extends across approximately one half of the bridge. In addition, the lower, radially inward corner of the intersection of the leg 140 and handle 142 connects along an arcuate web portion 188 to the outer side of the first vertical section 174 of the closure 134. The leg 140 thus connects to the closure 134 via the thinned webs 187 and 188 on three sides, and on its top edge is integrally formed with the bridge 180.

Figure 10B:
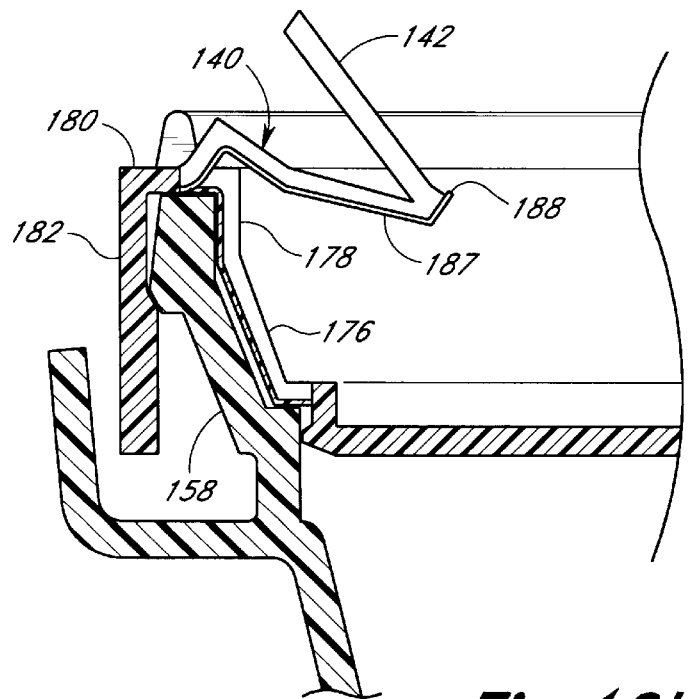
FIG. 10b is a cross-sectional view of the upper container rim as in FIG. 10a illustrating a pull-tab having been lifted from an initial position during removal of the closure from the container.

The disposition of the pull-tab 138 after having been severed along its three web sides is seen in FIG. 10*b*. To open the closure 134, one grasps the handle 142 and pulls the pull-tab 138 upward to first sever the web portion 188, and then simultaneously sever the parallel webs 187. The handle 142 includes a small nub 190 on its distal end, as seen in FIGS. 8 and 9, to help ensure good grip for the user. The nub 190 is representative of a number of variations to provide better grip on the handle 142, such as a plurality of nubs, a roughened region, a T-structure, and even a ring on the end of the handle.

Once the leg 140 has been fully separated from the closure 134 except at its line of connection to the bridge 180, further pulling on the pull-tab 138 lifts the closure 134 at that circumferential location and forces the skirt 184 over the circular rib 160. Once a portion of the skirt 184 has cammed over the rib 160, the closure 134 easily pulls off of the container 132. Again, prying of the closure 134 by the fingers or with the use of other tools is made extremely difficult by the protection of the lower edge of the skirt 184 with the outer flange 168. If anyone attempts to remove the closure 134 without the use of the pull-tab 138, damage to the container 132 or closure is likely to result, providing evidence of tampering. Moreover, with the highly visible location of the webs 187 and 188, one cannot use the pull-tab 138 to remove the closure 134 and later conceal the tampering. The webs 187 and 188 plastically stretch and cannot be reconditioned with glue or any other such means into their original state.

The sealing ring 172 enables the closure 134 to be removed by the pull-tab 138, and then replaced over the container mouth and sealed to preserve the freshness of the contents of the container. The combination of the tamper-evident closure 132 and the capacity to reseal the closure after the initial removal is a major advantage over previous closure systems. Also, the closure can easily be reopened using the pull-tab 138.

Another advantage of the preferred tamper-evident container system 130 is the nearly vertical angle that the handle 142 forms with the leg 140. The previously described poppet-style mold assembly 100 is preferably used to allow the undercut pull-tab handle 138 to be extracted from the mold without rupture. The step of removing the closure 134 from the mold cavity poppet 106, causes the handle 138 to flex around the outer periphery of the poppet. This is seen in FIGS. 6 and 7.

The nearly vertical angle that the handle 142 makes with the leg 140 reduces the amount of bending stress at their juncture, thus reducing the potential for structural cracking. The angle theta (θ) from the horizontal, seen in FIG. 10a, is preferably at least 60°, and more preferably is at least 75°, to ensure that no cracking of the pull-tab junction will occur. Because of the sharp upward angle that the handle 138 makes, and the shallow nature of the recess in the top of the closure, the handle juts upward and then circumferentially sideways to generally conform to the inner wall of the recess. Of course, those of skill in the art will recognize that other arrangements of the handle are possible.

Although this invention has been described in terms of certain preferred embodiments, other embodiments that will be apparent to those of ordinary skill in the art are intended to be within the scope of this invention. For example, the tamper-evident container system disclosed herein may be adapted to protective caps for the ends of tubular glass, metal, or plastic products. Furthermore, the improved closure may be used for metal, canned nonvacuum products, water-based household paint containers, and composite material cans. Accordingly, the scope of the invention is intended to be defined by the claims that follow.

What is claimed is:

1. A closure for use on a tamper-evident container having an opening and a lip surrounding the opening, the closure comprising:
    a bridge on the closure which covers the container lip when the closure is covering the opening;
    a skirt which depends from the periphery of the closure bridge;
    a non-removable pull-tab on the closure and extending inwardly, the pull-tab joined to the closure by at least one leg; and
    a frangible web formed in the closure and beginning at the point where the leg is joined to the closure, the web extending at least partially across the bridge and adapted to tear upon pulling the pull-tab upwardly and outwardly so as to provide a visible indication that the closure has been removed without removing the pull-tab from the closure, wherein the pull-tab has at least one leg extending at least partially across the bridge and having approximately the same thickness as the bridge so as to form a continuation of the bridge profile, and the web joins the leg on both sides to the bridge.

2. The apparatus of claim 1, wherein the web has a thickness less than about ¼ the thickness of the leg.

3. The apparatus of claim 1 wherein the pull-tab extends inwardly from said closure at an angle with the horizontal of at least 60°.

4. The apparatus of claim 3 wherein the angle is at least 75°.

5. The apparatus of claim 3 wherein the closure defines a peripheral rim having an inner wall and said bridge.

6. The apparatus of claim 5 wherein the pull-tab further includes a handle extending along a circumferential portion of said inner wall.

7. The apparatus of claim 5 wherein when the closure is in its initial, unopened state, the pull-tab does not extend above the peripheral rim.

8. A tamper-evident container and closure, comprising:
    a container having an upper lip which surrounds an opening in the container;
    an outwardly extending shelf surrounding the periphery of the container and joined to the container proximate to the container lip;
    an upwardly extending flange joined to the shelf and spaced from the container;
    a closure which covers the opening in the container;
    a peripheral rim, a bridge and an outer wall on the closure combining to removably secure the closure on the container lip when the closure is covering the opening, the outer wall depending from the bridge and fitting between the container lip and the flange, a bottom edge of the outer wall terminating proximate to the shelf so that the bottom edge of the outer wall cannot be easily manually engaged to remove the closure from the container;
    a pull-tab on the closure and extending inwardly from the peripheral rim, the pull-tab joined to the closure by at least one leg; and
    a frangible web formed in the closure and beginning at the point where the leg is joined to the closure, the web extending at least partially across the bridge of the rim, the web being adapted to tear upon pulling the pull-tab upwardly and outwardly so as to provide a visible indication that the closure has been removed, the pull-tab being connected to the closure so as not to separate from the closure upon tearing of the web and removal of the closure from the container, wherein the pull-tab is substantially U-shaped and is joined to the closure by two legs and wherein a web is provided on both sides of each leg.

9. The apparatus of claim 8 wherein when the closure is in its initial, unopened state, the pull-tab does not extend above the peripheral rim.

10. The apparatus of claim 8 wherein the web extends through the peripheral rim and terminates at a point spaced from the bottom edge of the outer wall.

11. The apparatus of claim 8 wherein the pull-tab attaches to a lower portion of the rim and extends inwardly at an angle with the horizontal of at least 60°.

12. The apparatus of claim 6 wherein said angle is at least 75°.

13. The apparatus of claim 11 wherein the pull-tab further includes a handle extending along a circumferential periphery of said rim.

14. The apparatus of claim 13 wherein when the closure is in its initial, unopened state, the pull-tab does not extend above the peripheral rim.

15. The apparatus of claim 8 wherein the shelf and flange extend uninterrupted around the entire periphery of the container.

16. The apparatus of claim 8 wherein the closure further comprises a sealing ring which sealingly engages the container so that the closure may be used to reseal the container after opening.

17. The apparatus of claim 8 wherein the closure further comprises a solid central portion recessed below the peripheral rim, the pull-tab extending from the peripheral rim above the central portion.

18. The apparatus of claim 17 wherein the closure further comprises a sealing ring formed on the periphery of the central portion and below a point of attachment between the pull-tab and closure, the ring sealingly engaging the container so that the closure may be used to reseal the container after opening.

19. The apparatus of claim 8 wherein the closure further includes an inner wall connected to said bridge opposite said outer wall.

20. A closure for use on a tamper-evident container having an opening and a lip surrounding the opening, the closure comprising:

a bridge on the closure which covers the container lip when the closure is covering the opening;

a downwardly extending wall portion having one side connected to the bridge and the opposing side connected to a sealing ring that is configured to engage and seal the opening when the closure is placed on the container;

a non-removable pull-tab on the closure and extending inwardly, the pull-tab joined to the wall portion by at least one leg; and a frangible web formed in the wall portion where the leg is joined, the web extending at least partially across the bridge and adapted to tear the wall portion upon pulling the pull-tab upwardly and outwardly so as to provide a visible indication that the closure has been removed without separating the closure into multiple pieces, wherein the pull-tab has at least one leg extending at least partially across the bridge and having approximately the same thickness as the bridge so as to form a continuation of the bridge profile, and the web joins the leg on both sides to the bridge.

21. The apparatus of claim 20, wherein the web has a thickness less than about ¼ the thickness of the leg.

22. The apparatus of claim 20, wherein the pull-tab has an elongated member that extends along a peripheral portion of the opening and extends inwardly from said closure at an angle with the horizontal of at least 60°.

23. The apparatus of claim 22, wherein the angle is at least 75°.

24. A closure for use on a tamper-evident container having an opening and a lip surrounding the opening, the closure comprising:

a bridge on the closure which covers the container lip when the closure is covering the opening;

a skirt which depends from an outer periphery of the closure bridge on an outside of the opening, the skirt having a sealing surface located on an inner surface of the skirt and positioned to engage and seal with an outwardly extending sealing surface on the container;

a downwardly extending wall portion having one side connected to an inner periphery of the bridge and the opposing side connected to a sealing ring that is configured to engage and seal the opening when the closure is placed on the container;

a non-removable pull-tab on the closure, the tab extending inwardly along and adjacent to a portion of the wall portion, the pull-tab joined to the wall portion by at least one leg; and a frangible web formed in the wall portion where the leg is joined, the web adapted to tear the wall portion upon pulling the pull-tab upwardly and outwardly so as to provide a visible indication that the closure has been removed without removing the pull-tab from the closure, the web not extending a distance to permit separation of the closure into multiple pieces.

* * * * *